United States Patent [19]
Kwun et al.

[11] Patent Number: 5,581,037
[45] Date of Patent: *Dec. 3, 1996

[54] NONDESTRUCTIVE EVALUATION OF PIPES AND TUBES USING MAGNETOSTRICTIVE SENSORS

[75] Inventors: Hegeon Kwun, San Antonio; Cecil M. Teller, II, Austin, both of Tex.

[73] Assignee: Southwest Research Institute, San Antonio, Tex.

[ * ] Notice: The term of this patent shall not extend beyond the expiration date of Pat. No. 5,456,113.

[21] Appl. No.: 401,170

[22] Filed: Mar. 9, 1995

Related U.S. Application Data

[63] Continuation-in-part of Ser. No. 973,152, Nov. 6, 1992, Pat. No. 5,456,113, and Ser. No. 33,256, Mar. 16, 1993, Pat. No. 5,457,994, which is a continuation-in-part of Ser. No. 973,152.

[51] Int. Cl.$^6$ .......................... G01N 29/14; G01N 29/28
[52] U.S. Cl. .................. 73/623; 73/622; 73/643; 324/242; 324/240; 324/220
[58] Field of Search .................. 73/587, 622, 623, 73/592, 598, 643, 597, 594, 779; 324/242, 220, 240

[56] References Cited

U.S. PATENT DOCUMENTS

| | | | |
|---|---|---|---|
| 3,115,774 | 12/1963 | Kolb | 73/151 |
| 3,311,818 | 3/1967 | Quittner | 324/34 |
| 3,427,872 | 2/1969 | Leep et al. | 73/88.5 |
| 3,555,887 | 1/1971 | Wood | 73/643 |
| 3,850,028 | 11/1974 | Thompson et al. | 73/643 |
| 4,092,868 | 6/1978 | Thompson et al. | 73/643 |
| 4,104,922 | 8/1978 | Alers et al. | 73/643 |
| 4,295,214 | 10/1981 | Thompson | 73/643 |

(List continued on next page.)

FOREIGN PATENT DOCUMENTS

| | | | |
|---|---|---|---|
| 0083654 | 4/1987 | Japan | 73/594 |
| 1507940 | 9/1989 | U.S.S.R. | 73/594 |

OTHER PUBLICATIONS

Josef Krautkramer and Herbert Krautkramer Mar. 1977 Ultrasonic Testing of Materials, Chapter 8, "Other Methods for Transmitting and Receiving Ultrasound", Second Edition, pp. 150–172.

J. Szilard 1982 Ultrasonic Testing: Non-conventional testing techniques, Chapter 9, "Techniques using dry coupling or non-contact coupling," (John Wiley & Sons), pp. 381–409.

Benson Carlin 1960 Ultrasonics, Chapter 4, "Magnetostriction," Second Edition, (McGraw-Hill Book Company, Inc.) pp. 93–125.

Primary Examiner—Hezron E. Williams
Assistant Examiner—Rose M. Finley
Attorney, Agent, or Firm—Gunn, Lee & Miller, P.C.

[57] ABSTRACT

A method and apparatus for the inspection of ferromagnetic and non-ferromagnetic pipes, tubes or other cylindrical shell structures utilizing the magnetostrictive effect to detect defects such as corrosion pits, wall thinning, and cracks within the structure under evaluation. The apparatus and method constitute an active testing application, wherein 1) a transmitting coil element generates a mechanical pulse within a cylindrical shell structure through the magnetostrictive effect and a second coil detects reflected mechanical waves within the pipe, this by the inverse magnetostrictive effect, or 2) a single sensor functions as both transmitter and detector. The present invention also anticipates a passive monitoring application with a detection coil that continuously monitors ferromagnetic or non-ferromagnetic tubes, pipes, etc., for mechanical or acoustic wave emissions and either records this monitored information or alerts the appropriate personnel to the existence of mechanical or acoustic wave emissions indicative of deterioration. Non-ferromagnetic pipes, tubes, etc., are made amenable to inspection by attaching a layer of ferromagnetic material such as nickel on either the inner or outer walls of the pipes, tubes, etc. by plating or bonding such material in a local area where the sensor is to be placed.

14 Claims, 4 Drawing Sheets

U.S. PATENT DOCUMENTS

| | | | |
|---|---|---|---|
| 4,296,486 | 10/1981 | Vasile | 73/643 |
| 4,307,616 | 12/1981 | Vasile | 73/643 |
| 4,309,903 | 1/1982 | Ono | 73/587 |
| 4,352,038 | 9/1982 | Moreton | 73/587 |
| 4,353,255 | 10/1982 | Fukuda | 73/587 |
| 4,380,931 | 4/1983 | Frost et al. | 73/643 |
| 4,395,913 | 8/1983 | Peterson | 73/643 |
| 4,408,160 | 10/1983 | King et al. | 324/209 |
| 4,420,978 | 12/1983 | Robinson et al. | 73/643 |
| 4,459,851 | 7/1984 | Crostack | 73/587 |
| 4,593,565 | 6/1986 | Chamuel | 73/643 |
| 5,456,113 | 10/1995 | Kwun et al. | 73/587 |

NONDESTRUCTIVE EVALUATION OF PIPES AND TUBES USING MAGNETOSTRICTIVE SENSORS

This application is a Continuation in Part of application Ser. No. 07/973,152, filed Nov. 6, 1992, now U.S. Pat. No. 5,456,113, and application Ser. No. 08/033,256, filed Mar. 16, 1993, now U.S. Pat. No. 5,459,994, which is a continuation in part of Ser. No. 07/973,152.

BACKGROUND OF THE INVENTION

1. Field of the Invention

The present invention relates generally to non-destructive testing (NDT) of pipes, tubes, and other cylindrical shell structures for flaws and fractures. The present invention relates more specifically to a non-destructive evaluation (NDE) system and method for flaw detection in pipes, tubes, and other cylindrical shell structures using magnetostrictively generated mechanical waves and magnetostrictively detected mechanical waves reflected from flaws.

2. Description of the Related Art

Pipes, tubes, and other cylindrical shell structures are important components in a variety of industries, including the power generating, pipeline, and petrochemical industries. The failure of pipelines and other such conduits associated with these industries can often be disastrous, leading to the loss of operating revenue, extensive structural damage, environmental contamination, unscheduled plant shut-downs, and in extreme cases even the loss of life. The inspection of such pipes, tubes, and conduits is, therefore, an essential part of system maintenance procedures in each of these industries.

At present, various inspection techniques that include ultrasonic, eddy current, x-ray, and magnetic flux leakage methods, are used for such pipeline, tube, and conduit inspections. In general, these techniques are well suited for localized inspections, as for example, the inspection of individual welded areas. However, for situations where defects can occur at any place in a long pipe or tube (for example, in pipes under thermal insulation or wrapping in petrochemical processing plants), or where the number of pipes to be inspected is large (for example, in steam generators and boilers), inspection using any of these techniques can be very time consuming and expensive. In such cases, inspections are very often performed only on a select portion of the pipes as a sample intended to be indicative of the overall condition of the entire group. This may or may not be satisfactory for assuring system safety and reliability and merely reduces the risk of failure a small degree.

As an example of current methods, gas pipelines, which generally extend over hundreds of miles, are sometimes inspected for corrosion using a magnetic flux leakage "pig". Such methods are at best incomplete since the detection of cracks in gas pipelines using the magnetic flux leakage method is not particularly sensitive. Ultrasonic techniques, which might be sensitive enough to detect smaller cracks, are often difficult to apply to pipelines because of the transducer couplant requirements.

Magnetostrictive sensor technologies remove many of the above described disadvantages of conventional NDE techniques and can significantly improve the efficiency of inspection. The salient features of the present invention that derive from the use of a magnetostrictive sensor system include the ability to; inspect 100% of the pipe cross-section, inspect long segments of pipe (more than 100 feet) from a single location, detect defects on both the outside and inside diameter surfaces of the pipe, function without need for a couplant, and operate at a low cost of inspection.

Magnetostrictive sensors may be applied either from the outside diameter of the pipe or, in appropriate situations, on the inside diameter of the pipe. Normally, magnetostrictive sensors are most easily applied to pipes, tubes, and other cylindrical shell structures that are made of ferromagnetic materials. However, for many non-ferrous pipes, tubes, etc. (Inconel steam generator tubes for example), magnetostrictive sensors can still be utilized by plating or bonding thin layers of magnetizable materials, such as nickel, on the pipe or tube in a localized area where the sensor is to be placed. In this way, the methods involved in magnetostrictive wave generation and detection can be utilized in association with both ferrous and non-ferrous pipes, tubes, and cylindrical shell structures.

Applicant's co-pending patent applications Ser. Nos. 07/973,152 and 08/033,256 describe in greater detail various methods for utilizing magnetostrictively generated waves and magnetostrictively detected waves in long, solid, cylindrical structures such as cables and ropes. Hollow cylindrical structures such as pipes, tubes, etc., present specific geometric and wave propagation characteristics that require some modification of the methods and devices associated with magnetostrictive non-destructive evaluation. Heretofore, little effort has been made to develop such methods and devices appropriate for the magnetostrictive analysis of hollow cylindrical shell structures.

Background on the Magnetostrictive Effect

The magnetostrictive effect is a property that is peculiar to ferromagnetic materials. The magnetostrictive effect refers to the phenomena of physical dimensional change brought about through variations in magnetization.

In magnetostrictive sensor applications, the generation and detection of mechanical waves is typically achieved by introducing a pulsed current into a transmitting coil adjacent a ferromagnetic material. A change in magnetization within the material located near the transmitting coil causes the material to change its length locally in a direction parallel to the applied field. This abrupt local dimensional change, which is the magnetostrictive effect, generates a mechanical wave that travels at the speed of sound within the material. When the mechanical wave is reflected back from the end of the material, or from a defect in the material, and reaches a detection coil, which is in many respects similar to the transmitting coil, it generates a changing magnetic flux in the detection coil as a result of the inverse magnetostrictive effect. This changing magnetic flux in turn induces an electric voltage within the detection coil that is proportional to the magnitude of the mechanical wave.

The advantages of utilizing the magnetostrictive effect in NDE applications include the sensitivity of magnetostrictive sensors, the durability of such sensors, the lack of the need for a sensor/material couplant, the long range of the mechanical waves involved, the ease of implementation, and the low cost of both the sensors and the system electronics.

SUMMARY OF THE INVENTION

It is, therefore, an object of the present invention to provide an apparatus and method for the non-destructive evaluation of ferromagnetic and non-ferromagnetic pipes, tubes, and other cylindrical shell structures to detect material flaws, such as corrosion pits and cracks.

It is another object of the present invention to provide an apparatus and method for the passive monitoring of ferromagnetic and non-ferromagnetic pipes, tubes, and other cylindrical shell structures that utilizes the magnetostrictive effect to detect mechanical waves from progressing cracks or fractures.

Accordingly, the present invention provides an apparatus and method for utilizing the magnetostrictive effect to generate and to detect mechanical waves in ferromagnetic and non-ferromagnetic cylindrical shell structures. The sensors for generating and detecting these mechanical waves in the walls of a cylindrical shell structure consist of two general elements; a) an electronically conductive coil of predetermined number of turns, length, and diameter, and b) a means for providing a DC bias magnetic field. The bias magnetic field is applied to enhance the efficiency of converting electrical energy to mechanical energy or vice-versa and to make the frequency of the electrical signals and mechanical waves the same.

Figure 1:
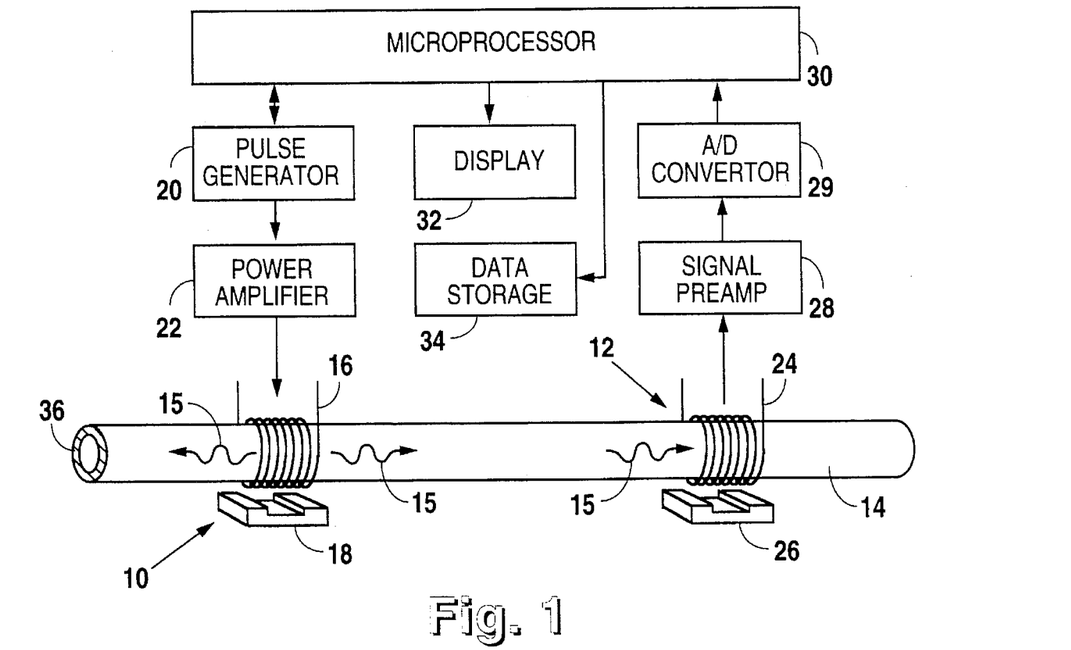
FIG. 1 is a schematic representation of the test apparatus of the present invention appropriate for the active magnetostrictive generation and detection of mechanical waves within a tube, pipe, or other cylindrical shell structure.

One application of the present invention, as shown in FIG. 1, involves encircling a tubular structure under inspection with a coil and energizing the coil with a pulsed electric current so as to induce and transmit mechanical waves (by way of the magnetostrictive effect) within the cylindrical shell wall of the pipe or tube. The mechanical waves result from a change of magnetization within the ferromagnetic material located within a space adjacent to the transmitting coil during the time period of the pulsed current. This change in magnetization causes a localized area within the ferromagnetic material to change in dimension and, as a result, to generate a mechanical wave of acoustic or ultrasonic frequencies that simultaneously travels along the cylindrical wall in both directions. When this mechanical wave is reflected back from the ends of the pipe or tube, or from areas within the pipe or tube with fractures or other anomalies that might reflect or impede the wave, it is returned to a detection coil where it generates a changing magnetic flux as a result of the inverse magnetostrictive effect. This changing magnetic flux in turn induces an electric voltage in the detection coil that is proportional to the magnitude of the reflected mechanical wave.

Figure 2A:
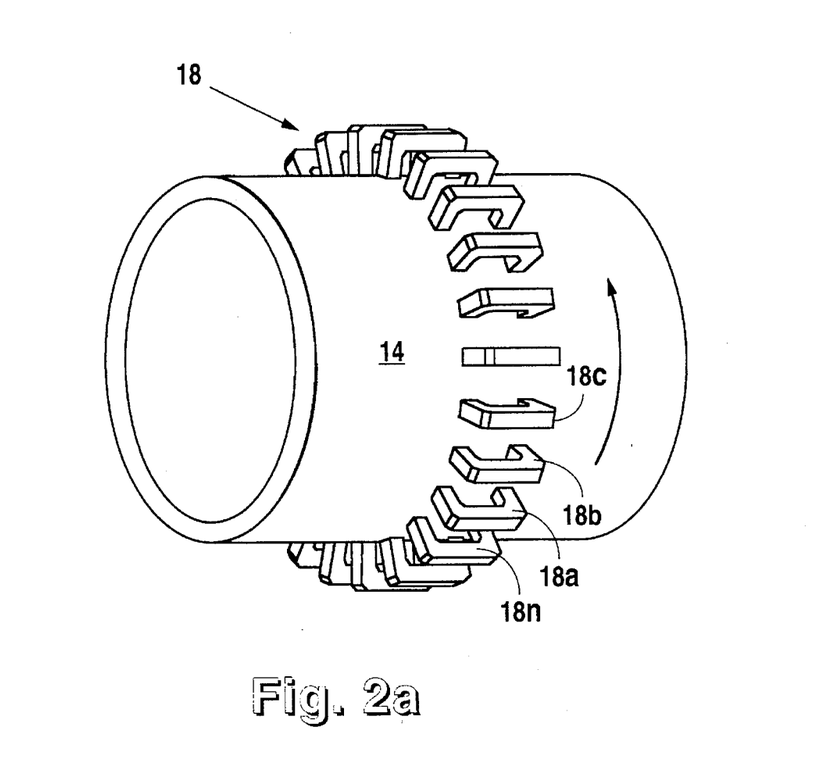
FIG. 2a is a perspective view of an array of DC bias magnetic modules of the present invention arranged circumferentially around a cylindrical shell structure.

To provide a DC bias magnetic field in the present invention, either electromagnets or permanent magnets may be used. To facilitate installation of the sensors for inspection of pipes or tubes from the outside, the present invention utilizes a quickly installable and removable external coil. The external coil consists of a ribbon cable of a predetermined number and length of electrical conductors, terminated with connecting pins. The individual conductors of the ribbon cable are arranged in such a way that when the connecting pins are engaged, the ribbon forms a continuous single conductor coil. This type of coil may be used for both sensor coils and for providing a DC bias magnetic field. When permanent magnets are used to provide the DC bias magnetic fields, an array of separate magnetic modules arranged around the circumference of the pipe is preferred, as shown in FIG. 2a. For ease of handling, these magnetic modules are designed so that their magnetic output may be turned on and off.

The method of the present invention involves amplifying, processing, displaying and analyzing the detected signal to identify, distinguish, and describe defects of concern. Sufficient experimental use with known anomalies and flaws in a specific pipe or tube structure can serve to establish an appropriate database and information baseline for the identification of the specific characteristics of anomalies, cracks, corrosion, etc. that are commonly seen within such pipes or tubes.

The apparatus and method of the present invention may also be applied in a passive mode to monitor mechanical waves emitted from the progressive growth of cracks in pipes, tubes, etc. Such a passive mode application would serve as a long-term monitoring means capable of recording information on detected mechanical wave emissions or capable of transmitting an alarm on the occurrence of a mechanical wave emission exceeding specified levels.

The geometry of the structures to which the apparatus and method of the present invention can be applied is generally not limited, but the following description of the present invention lends itself most effectively to the NDE of elongated cylindrical structural elements.

DETAILED DESCRIPTION OF THE PREFERRED EMBODIMENT

Reference is made first to FIG. 1 for a detailed description of the arrangement of a test apparatus appropriate for implementation of the method of the present invention, providing for the generation and detection of mechanical waves within a cylindrical shell wall from outside of the cylindrical shell structure. In this active testing embodiment of the present invention, both a transmitting element (10) and a detection element (12) are required. The specific structures of transmitting and detection elements (10) and (12) are discussed in more detail below with regard to FIGS. 2b and 2c.

While no direct mechanical coupling to pipe (14) under examination is required, elements (10) and (12) must be arranged adjacent to the ferromagnetic tube, pipe, or other cylindrical shell structure (14). Transmitting and detection elements (10) and (12) can be operated at a distance of more than several centimeters from the ferromagnetic material. It should be noted again that the testing of non-ferromagnetic pipes, tubes, etc., can be accomplished by positioning ferromagnetic material, such as metallic banding or plating, in mechanical contact with pipe or tube (14) and then placing elements (10) and (12) of the present invention proximate to the ferromagnetic material. As long as mechanical waves may travel between the ferromagnetic material thus attached and pipe or tube (14), appropriate analysis and evaluation can be carried out.

Transmitting element (10), positioned adjacent to pipe (14) under evaluation is comprised primarily of transmitting coil (16) and bias magnet (18). A pulse or tone burst generator (20) is coupled through power amplifier (22) to transmitting coil (16) and generates a signal appropriate to effect a mechanical wave (15) within material (14) under evaluation.

Detection element (12) of the apparatus of the present invention is configured much like transmitting element (10) and is comprised primarily of detection coil (24), also positioned adjacent to pipe specimen (14) under evaluation, as well as bias magnet (26). The signals generated by detection coil (24) in response to the passage of mechanical wave (15), are conditioned by signal pre-amp (28) and A/D convertor (29). The digital signal is then presented to microprocessor (30) at which point it may be displayed directly on associated display means (32) or stored in memory (34) for later review and analysis.

Mechanical waves propagating in a cylindrical shell will generally exhibit a dispersion. That is, different frequency components of the waves will propagate at different velocities. As a result, a mechanical pulse, which might contain a wide range of frequency components, disperses over time. This dispersion creates many undesirable signals that interfere with the detection of signals reflected from defects. This problem can be minimized by energizing transmitting coil (10) with a tone burst of a single frequency electric current. In addition, to reduce the generation of different wave modes by transmitting coil (10), the DC bias magnetic field created by bias magnet (18) should be relatively uniform around the circumference of pipe (14). This can be effected by using an array of bias magnetic modules as described with regard to FIG. 2a.

Bias magnets (18) and (26) need not be present in every case if, for example, sufficient residual magnetization is left in material (14) under study. This may often be true in the case of highly ferrous pipe structures such as cast-iron or steel pipes. In addition, the representation of bias magnets (18) and (26) in FIG. 1 are intended to be schematic and could in fact be structured in any of a number of configurations with both permanent magnets and/or electromagnets.

The arrangement for inspection of cylindrical shells from the inside diameter of the shell is very much similar to that for inspection from the outside as described above. In this inside diameter case, the transmitting and detection coils are wound on a plastic bobbin whose diameter is somewhat smaller than the inside diameter of the cylindrical shell. The bias magnet modules in this case are positoned about the inside diameter surface of the cylindrical shell.

The method of the present invention, as applied to the combined generation and detection of mechanical waves within a material, is generally directed to carry out the analysis on a test-by-test basis. Defect detection in the preferred embodiment is fundamentally based upon the pulse-echo technique. Defect detection and analysis for pipe or cylindrical structure (14) is accomplished by identifying mechanical waves (15) that are reflected from defects within the pipe. These reflected waves result from acoustic impedance changes as the incident waves encounter the defects. Inspection techniques other than pulse-echo, such as "pitch-catch" or "through-transmission" can also be used for defect detection in the non-destructive evaluation of the pipe condition.

Both the transmission and detection of mechanical waves (15) are accomplished without the use of a couplant, such as water or oil, that is normally required for other NDE techniques such as ultrasound. Sensor (12) can be operated at a substantial gap, sometimes with more than several centimeters between the element and the pipe surface. In addition, with appropriate system electronics, it is possible to use a single magnetostrictive element for both the transmission and the detection of mechanical waves (15).

Transmitting magnetostrictive element (10) consists of two basic components: a) a means for producing a variable magnetic field and b) a means for statically magnetizing the pipe wall. Likewise, detection magnetostrictive sensor element (12) generally consists of two basic components: a) a means for detecting magnetization changes occurring in the pipe wall due to the mechanical wave, and b) a means for statically magnetizing the pipe wall. For both transmitting and detection elements (10) and (12), an inductive coil (16) in transmitting element (10), and (24) in sensor element (12), is used to produce a variable magnetic field and to detect the magnetization changes in material (14). Detection element (12), may in some situations, be based on other types of magnetization sensing devices such as hall effect probes.

For statically magnetizing pipe wall (36), a permanent magnet (18), in element (10), and (26) in element (12), is used, and is physically placed in a configuration suitable for direct magnetic association with transmitting coil (16) or detection coil (18), as the case may be. Physically, permanent magnets (18) and (26) can be either combined with or separated from the means for producing or detecting the magnetic flux. In addition, instead of permanent magnets (18) and (26), either electromagnets or residual magnetization in material (14) can be used. Residual magnetization can be established in pipe wall (36) by magnetizing material (14) using a magnet (permanent or electric) and then removing the magnet. This is a preferred method when appropriate because the need for installing a magnet (permanent or electric) together with transmitting and detection elements is eliminated.

The reasons for keeping material (14) magnetized are two-fold: a) to enhance the conversion efficiency of transmitter coil (10) and detection coil (12) from electrical energy to mechanical energy or vice-versa, and b) to make the frequency response of magnetostrictive elements (10) and (12) linear. If material (14) demagnetizes, the frequency of the detected signal would be twice the frequency of mechanical wave (15) or the frequency of the generated mechanical wave will be twice the frequency of the applied electric current.

Using magnetostrictive transmitters and detectors, three different wave modes can be generated and detected in a pipe. These wave modes can be generally described as longitudinal, torsional and flexural. For defect detection and analysis, the wave modes of most value are typically longitudinal and torsional waves. In general, longitudinal waves are best used for the detection of circumferentially oriented cracks and wall thinning in a pipe due to corrosion, while torsional waves are best used for the detection of longitudinally oriented cracks and wall thinning. The sensor configuration described in FIG. 1 is best suited for the generation and detection of longitudinal wave modes. The use of torsional waves is more limited because of the difficulty associated with generating a pure torsional wave mode without simultaneously generating other wave modes which interfere with defect detection.

Figure 2B:
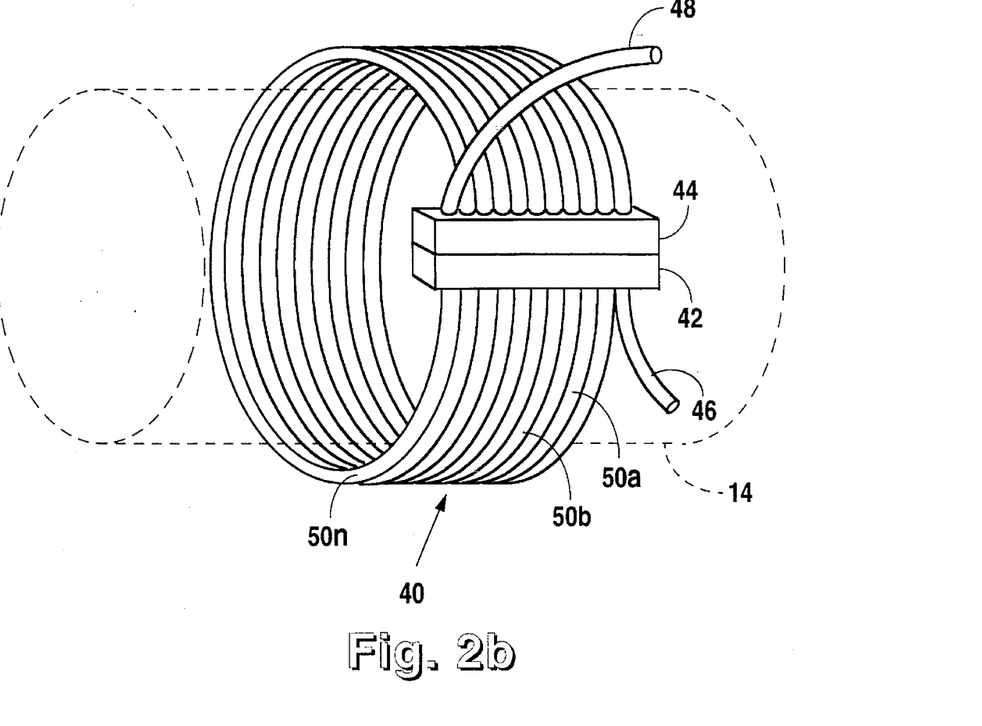
FIG. 2b is a perspective view of a ribbon cable means for establishing a conductive coil about the exterior surface of a cylindrical shell structure.
Figure 2C:
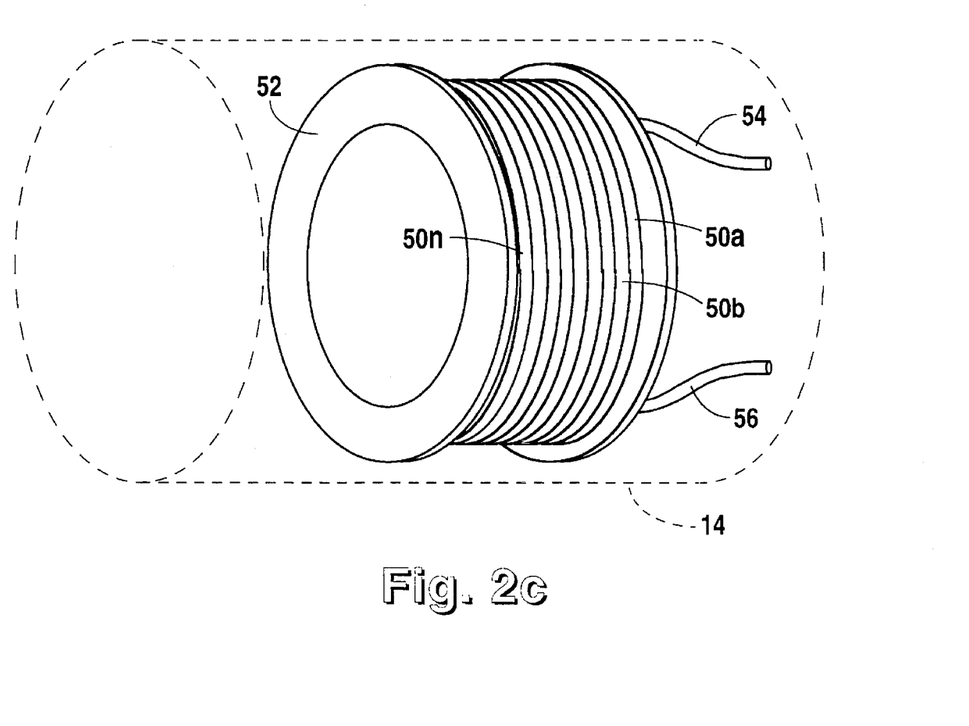
FIG. 2c is a perspective view of a bobbin-wound means for establishing a conductive coil within the interior surface of a cylindrical shell structure.

Reference is now made to FIGS. 2a–2c for a detailed description of the structural characteristics of magnetostrictive sensor coils and bias magnet configurations suitable for implementation in the system and with the method of the present invention. FIG. 2a shows an array of permanent magnets (18) positioned circumferentially about the outer surface of pipe (14). Array (18) is comprised of individual magnetic modules (18a, 18b, ... 18n) and is variable in size (length) according to the outside diameter of pipe (14). Magnetic module array (18) is structured such that more or fewer of the individual modules may be incorporated into the circumferential band surrounding the pipe.

This method of creating a bias magnetic field within the cylindrical shell wall is appropriate for use in conjunction with both internal and external sensor coil configurations. In some instances, such as with the inspection of buried pipelines from a "pig", it may be necessary to establish a DC bias magnetic field directly on the interior surface of the cylindrical shell structure wherein the arrangement shown in FIG. 2a may be reduced in size and reversed in orientation for insertion into an internal circumferential array of similar structural and functional fashion. For application of the present invention to the inspection of buried pipeline using a "pig" which traverses along the pipeline, bias magnet module (18) may need to be equipped with an array of wire brushes to minimize fluctuations in the DC bias magnetic field arising from the motion of the "pig". Such wire brush structures are routinely used for magnetic flux leakage inspections to acheive the same purpose.

FIG. 2b shows in more detail a magnetostrictive sensor coil appropriate for implementation in the present invention when the sensor is to be utilized on the external surface of the pipe to be examined. The objective of this structural configuration for the magnetostrictive sensor coil is ease of implementation on pipe diameters of varying size. Ribbon cable sensor (40) is comprised of a series of electrical conductors (50a–50n) which are typically insulated and molded together in a flat ribbon fashion. Conductors (50a–50n) are terminated at two points by connectors (42) and (44) which mate together again in standard fashion. Conductors (50a–50n) are, however, offset by one connection point within connectors (42) and (44) in a manner such that a single conductive path is created through what would otherwise be a plurality of short individual conductive closed circuits.

This arrangement creates a conductive coil with terminals (46) and (48) appropriate for use as an encircling coil of the type described above with respect to FIG. 1. It is anticipated that a number of standard-size ribbon cable coils of this structure could be utilized on various diameters of tubing and pipes. Because direct contact with the outer diameter surface of the pipe is not required, a ribbon cable coil sensor of a particular length could be utilized in conjunction with pipes having diameters over a moderate range of values. Three or four ribbon cable coils sensors of this type of increasing length might be used to cover a range of pipes from one or two inches in diameter to more than twelve or sixteen inches in diameter. In any case, the sensor structure shown in FIG. 2b provides an inexpensive mechanism for establishing a closed coil about an otherwise unaccessible outer circumference for a pipe.

It is understood that in some situations the cylindrical shell structure will have one end open and thus accessible for the application of any of a number of coil conductor structures. In most instances, however, it is anticipated that the cylindrical shell structure or pipe will have a very long dimension that would restrict the ability to attach a closed coil conductor. The structure disclosed in FIG. 2b is intended to overcome this problem.

FIG. 2c discloses a coil conductor structure designed to be inserted into the interior of a pipe or cylindrical shell structure and to be positioned proximate to the interior surface of the pipe. Bobbin (52) is dimensioned with a diameter close to, but less than, the inner diameter of the pipe under investigation. Unlike the coil conductor structure shown in FIG. 2b, the use of a magnetostrictive coil sensor on the interior of a pipe requires direct access to a terminal end of the pipe for insertion. The objective of bobbin (52) shown in FIG. 2c, therefore, is to position the plurality of conductive coils (50a–50n) as close to the inner surface of pipe (14) as practical and still allow for the easy movement of bobbin coil (52) in and out of pipe (14). As with the coil structure shown in FIG. 2b, the coil in FIG. 2c is terminated at conductors (54) and (56). To promote electromagnetic coupling of the coil to the pipe wall, which is outside the coil, bobbin (52) is preferably made of laminate steel or ferrite. Bobbin (52) and the pipe wall then form a small magnetic circuit which links the changes in magnetization in either bobbin (52) or pipe wall (14) and allows the coil to either apply a variable magnetic field to pipe (14) or to detect the magnetization changes in pipewall (14).

Reference is now made to FIGS. 3–6 for a detailed description of the type of data typically acquired through the use of the method and apparatus of the present invention. Each of the figures are graphic plots of signals received utilizing the method and system of the present invention, wherein the detected magnetostrictive sensor signal amplitude in volts is plotted on the vertical or "y" axis and a time value in milliseconds is plotted on the horizontal or "x" axis.

Figure 3:
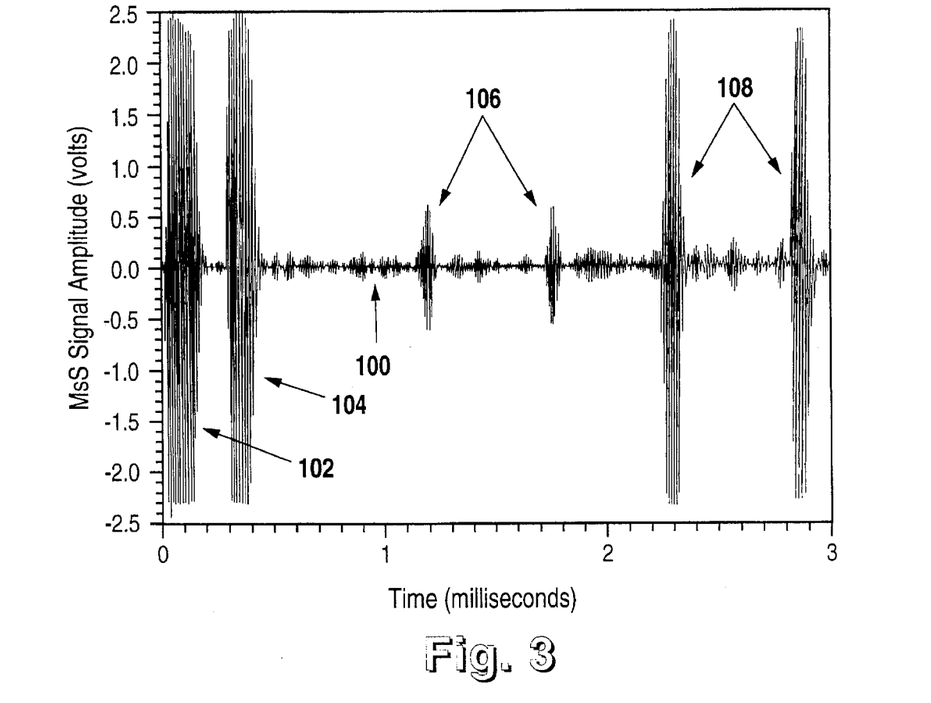
FIG. 3 is a generic graphic representation of an output signal obtained using the apparatus of the present invention on a long welded gas pipe section containing identifiable defects.

Reference is first made to FIG. 3 for a general description of the signal components typical of the present invention. In FIG. 3, signal 100 is comprised of six distinctive elements that are identifiable as events in the passage of mechanical waves within the cylindrical shell structure. The signal shown in FIG. 3 (and those in FIGS. 4–6) was acquired with a system structured much as that disclosed with respect to FIG. 1, wherein a distance exists between a coil for generating the mechanical waves and a coil for detecting the mechanical waves. Thus, as shown in FIG. 3, an initial pulse (102) is immediately followed by a second passing signal (104) whose separation from initial pulse (102) is an indication of the position of the generating and detecting coils. A similar pair of defect signals (106) follow thereafter, both of which are indicative of the same defect. The first defect signal is produced when the wave reflected from the defect passes the receiving coil on its return trip. The second defect signal is produced when the wave passes the receiving coil the second time on its outgoing trip after reflection from the sensor end of the pipe. Finally, end reflected or girth weld signals (108), as the case may be, indicate the end of the desirable window of investigation for the pipe. Here also, two end reflected signals are present because the same wave is detected twice, once during its return trip and the other during the outgoing trip after reflection from the sensor end of the pipe.

Figure 4:
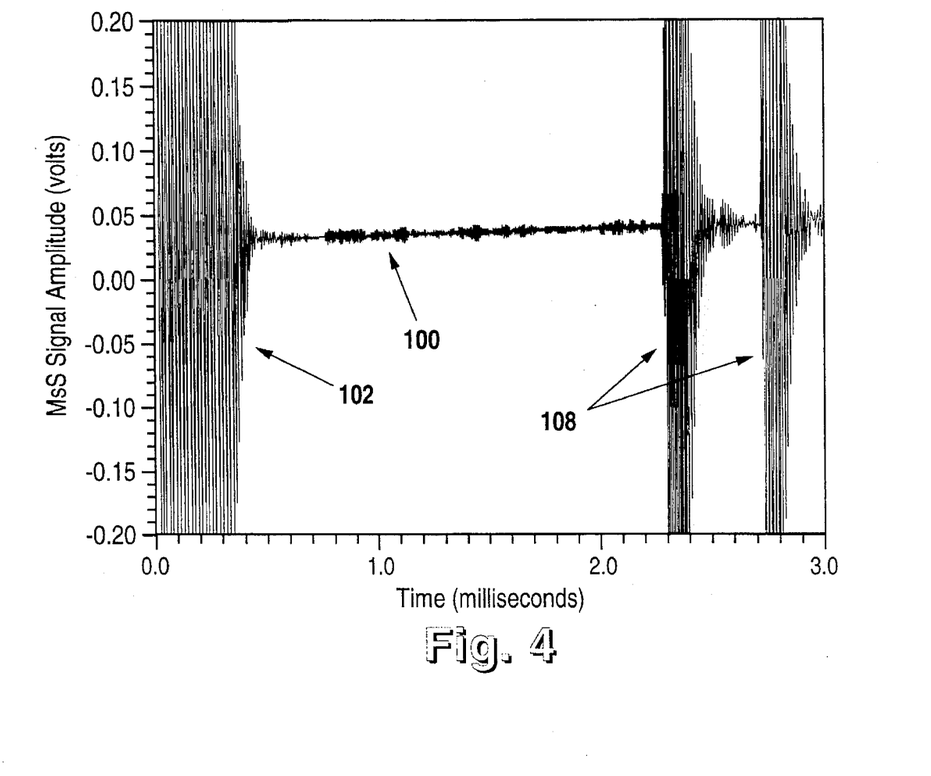
FIG. 4 is a graphic representation of an output signal obtained using the apparatus of the present invention on a 22 ft.-long steel walled pipe prior to inducing a defect therein.
Figure 5:
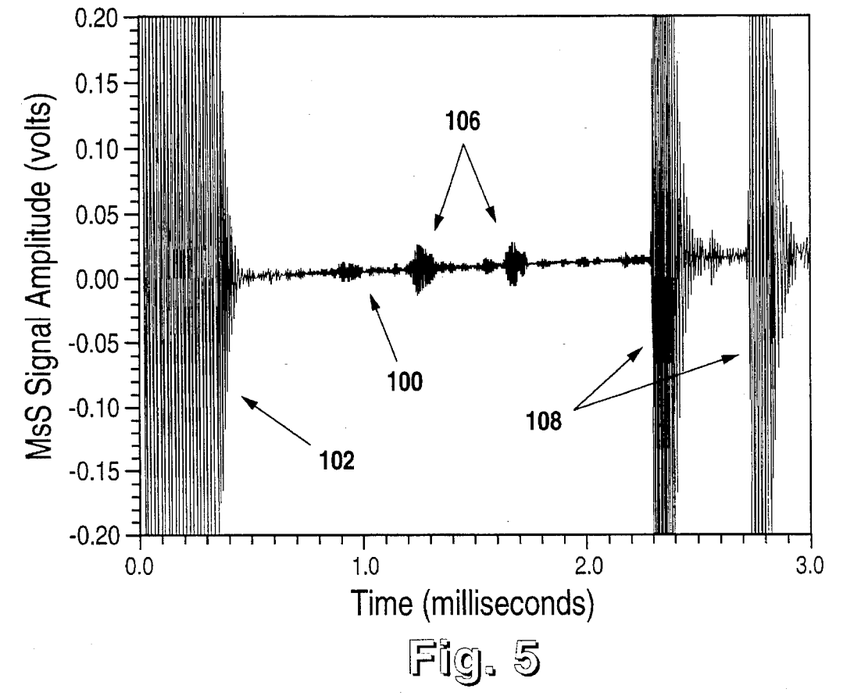
FIG. 5 is a graphic representation of an output signal obtained using the apparatus of the present invention with the same pipe structure used with FIG. 4 after introducing a moderate level defect in the pipe.
Figure 6:
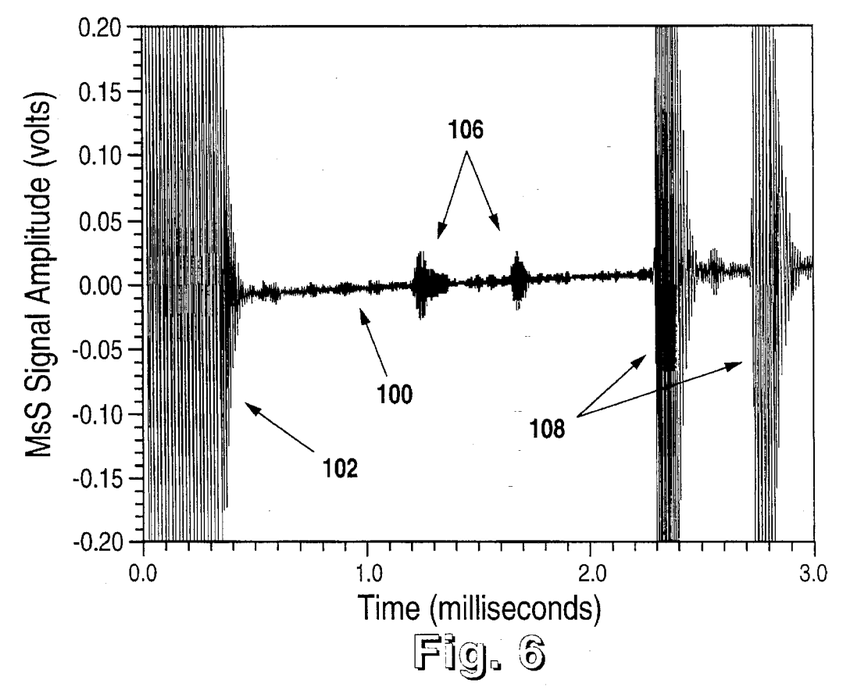
FIG. 6 is a graphic representation of an output signal obtained using the apparatus of the present invention with the same pipe structure used with FIGS. 4 and 5, but with a high level defect in the pipe.

FIGS. 4–6 display specific experimental data but still generally show each of the above-referenced signal components described generically in FIG. 3, with the exception of signal components (102) and (104) which are merged in FIGS. 4–6 because of the sensor placement. Initial pulse (102), therefore, shown in FIG. 4, contains the end reflected signal component shown as a discreet element (104) in FIG. 3.

The graphic representations shown in FIGS. 4–6 are based upon experimental data showing the detectability of corrosion-type defects in a 6⅝ inch outside diameter (OD) steel pipe using the magnetostrictive sensor techniques herein described. The pipe utilized was 22 ft. in length and was 0.188 inches in wall thickness. The transmitting magnetostrictive sensor was placed at about two inches from one end of the pipe and was excited with a 100 kHz tone burst. The detection magnetostrictive sensor was placed about 43 inches from the transmitting sensor.

Data acquired prior to inducing a defect in the pipe is shown graphically in FIG. 4. Here again, initial pulse (102) and two end reflected signals (108) are shown. As mentioned, initial pulse (102) includes the applied tone burst and the signal detected when the wave passed the detection sensor during its trip toward the far end of the pipe. The first of the end reflected signals (108) is the one detected during the return trip of the incident wave after reflection from the far end of the pipe. The second of the end reflected signals (108) is the one detected when the return wave made another round trip after reflection from the sensor end of the pipe. The two signals are thus separated by the round-trip time from the detection sensor to the sensor end of the pipe (in this case, approximately 0.45 milliseconds).

FIGS. 5 and 6 show signal data taken after a 0.5 inch diameter hole was induced on the pipe's outside diameter at a point approximately 148 inches from the sensor end of the pipe (or 103 inches from the detection sensor). The depth of the hole was approximately 0.058 inches for the data shown in FIG. 5 and 0.092 inches for the data shown in FIG. 6. The induced defects produce readily recognizable signals in the form of two defect signals (106) again because the wave is detected twice as described earlier. It is also evident from the difference in the amplitude of defect signals (106) disclosed between FIG. 5 and FIG. 6 that defect signal amplitude increases with the increasing depth of the hole. It has been experimentally demonstrated that a hole whose cross-section is as small as 0.25% of the total cross-section of the pipe can be detected using the instrumentation and the system of the present invention.

The signals acquired in FIGS. 4–6 were made utilizing externally placed coils in a manner similar to that shown in FIG. 1. Similar signal characteristics are evident from the use of both internally placed coils and various arrangements of DC bias magnet configurations.

It should also be noted that the inductive coil in the detection element can pick up stray electromagnetic waves which interfere with the magnetostrictive detection of mechanical waves. To reduce this electromagnetic interference (EMI), two approaches are used in the present invention. The first is the use of two inductive coils in the detection element which are separated by the half wavelength of the mechanical waves generated in the pipe wall. The outputs from these two coils are then input to a differential signal amplifier which inverts one of the inputs and adds the two input signals. The EMI signals then tend to cancel each other, while the signals due to the mechanical waves add each other. This results in a significant improvement in the signal to noise ratio of the detected mechanical wave signals. An alternative filtering approach could be used through a signal averaging process. Since the EMI signals are not synchronized with the timing of the energization of the transmitting coil, the averaging process also enhances the signal to noise ratio significantly.

While a number of applications of the preferred embodiments of the present invention have been identified, it is anticipated that one skilled in the art would identify further applications of each of these methods and each apparatus described, in a manner consistent with the procedures associated with the present invention. It is anticipated that the present invention would have applications in any environment where remote nondestructive evaluation of elongate cylindrical materials is required and a ferromagnetic substance is present, or may be introduced with little or no adverse effect.

We claim:

1. A method for the inspection of ferromagnetic cylindrical shell structures such as pipes and tubes, said cylindrical shell structure having a circumference and a length, to detect and locate fractures, cracks, and other anomalies, comprising the steps of:

establishing a first linearizing DC magnetic field in a first location, proximate to a surface of said shell structure and directed along said length of said cylindrical shell;

causing a fluctuation in said first magnetic field sufficient to generate a primary mechanical wave through a volume of said shell structure as a result of the magnetostrictive effect;

establishing a second linearizing DC magnetic field in a second location, proximate to a surface of said shell structure and directed along said length of said cylindrical shell;

detecting fluctuations in said second magnetic field as a result of a passage of said primary mechanical wave and a plurality of secondary mechanical waves through a volume of said shell structure, said fluctuations in said second magnetic field caused by an inverse magnetostrictive effect resulting from said passage of said mechanical waves through said second magnetic field, said plurality of secondary mechanical waves being generated and reflected by said fractures, cracks, and other anomalies in said shell structure;

analyzing said detected fluctuations in said second magnetic field indicative of said secondary mechanical waves and correlating said detected fluctuations with patterns of changes known to be indicative of said fractures, cracks, and other anomalies in said cylindrical shell structure.

2. The method of claim 1 wherein said step of establishing a first linearizing DC magnetic field comprises positioning a permanent magnet or electromagnet at said first location, proximate to a surface of said shell structure and orienting the poles of said permanent magnet or said electromagnet so as to direct said magnetic field along said length of said shell structure.

3. The method of claim 1 wherein said step of causing a fluctuation in said first magnetic field directed along a length of said shell structure, comprises placing an electromagnetic coil adjacent to said first location, proximate to a surface of said shell structure, and varying a current through said electromagnetic coil so as to produce magnetostrictive effects within a volume of said shell structure.

4. The method of claim 1 wherein said step of establishing a second linearizing DC magnetic field comprises positioning a permanent magnet or electromagnet at said second location, proximate to a surface of said shell structure and orienting the poles of said permanent magnet or said electromagnet so as to direct said magnetic field along said length of said shell structure.

5. The method of claim 1 wherein said step of detecting fluctuations in said second magnetic field directed along a length of said shell structure, comprises placing an electromagnetic detection coil at said second location, proximate to a surface of said shell structure, and detecting variations in a voltage induced in said electromagnetic coil caused by an inverse magnetostrictive effect within a volume of said shell structure.

6. An apparatus for the inspection of ferromagnetic cylindrical shell structures such as pipes and tubes, said cylindrical shell structures having a circumference and a length, to detect and locate fractures, cracks, and other anomalies, comprising:

a transmitting coil of at least one turn positioned adjacent to or encompassing a first location, proximate to a surface of said shell structure;

a first linearizing DC magnet adjacent said transmitting coil, said first DC magnet creating a first linear magnetic field within a volume of said shell structure and directed along said length of said cylindrical shell;

a signal generator and power amplifier capable of supplying said transmitting coil with a current sufficient to create fluctuations in said first magnetic field;

a detection coil of at least one turn positioned adjacent to or encompassing a second location, proximate to a surface of said shell structure and directed along said length of said cylindrical shell;

a second linearizing DC magnet adjacent said detection coil, said second DC bias magnet creating a second linear magnetic field within a volume of said shell structure;

a signal conditioner for amplifying and filtering a current within said detection coil, said amplified and filtered current being a signal indicative of fluctuations in said second magnetic field; and a display means for displaying said signal and for allowing a test operator to interpret said signal and thereby interpret said fluctuations in said second magnetic field;

wherein said fluctuations in said first magnetic field induce a magnetostrictive effect within a volume of said cylindrical shell structure and generate primary mechanical waves within said shell structure, and said fluctuations in said second magnetic field resulting from an inverse magnetostrictive effect caused by secondary mechanical waves within said shell structure, said secondary mechanical waves occurring as a result of said primary mechanical waves being reflected from said fractures, cracks, and other anomalies within said shell structure; and wherein said interpretation of said signal includes identifying a location and a degree of deterioration of said fractures, cracks, and other anomalies.

7. The apparatus of claim 6 further comprising recording means capable of receiving and storing said signal for subsequent display and interpretation.

8. The apparatus of claim 6 wherein said transmitting coil encompasses an exterior circumfrence of said structure.

9. The apparatus of claim 8 wherein said transmitting coil comprises a detachable conductor array with a first and a second matable ends, said conductor array capable of encircling said cylindrical shell structure by disconnecting said first and second matable ends and, after encircling said structure, connecting said matable ends to form a single conductor coil.

10. The apparatus of claim 6 wherein said transmitting coil is contained within an interior circumfrence of said structure.

11. The apparatus of claim 10 wherein said transmitting coil comprises a bobbin and a conductor wound about said bobbin, said bobbin dimensioned to be insertable within said structure.

12. The apparatus of claim 6 wherein said first DC bias magnet comprises a detachable magnetic module array with a first and a second matable ends, said array capable of encircling said cylindrical shell structure by disconnecting said first and second matable ends and, after encircling said structure, connecting said matable ends to form a continuous circle about said structure, said magnetic modules generating discrete, static magnetics fields within said structure.

13. The apparatus of claim 12 wherein said magnetic module array comprises discrete permanent magnets.

14. The apparatus of claim 12 wherein said magnetic module array comprises a series of electromagnetic coils.

* * * * *